(12) United States Patent
Baseeth et al.

(10) Patent No.: US 11,136,273 B2
(45) Date of Patent: Oct. 5, 2021

(54) LIQUID PRODUCTS HAVING INCREASED SOLIDS CONCENTRATIONS

(71) Applicant: Archer Daniels Midland Company, Decatur, IL (US)

(72) Inventors: Shireen S. Baseeth, Decatur, IL (US); Matthew Dyer, Mt. Zion, IL (US); John Less, Forsyth, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 455 days.

(21) Appl. No.: 15/537,723

(22) PCT Filed: Dec. 10, 2015

(86) PCT No.: PCT/US2015/064873
§ 371 (c)(1),
(2) Date: Jun. 19, 2017

(87) PCT Pub. No.: WO2016/105954
PCT Pub. Date: Jun. 30, 2016

(65) Prior Publication Data
US 2018/0271982 A1    Sep. 27, 2018

Related U.S. Application Data

(60) Provisional application No. 62/095,431, filed on Dec. 22, 2014.

(51) Int. Cl.
| | | |
|---|---|---|
| C05C 11/00 | (2006.01) | |
| C05G 3/50 | (2020.01) | |
| C05C 3/00 | (2006.01) | |
| C05G 5/23 | (2020.01) | |
| A23K 20/158 | (2016.01) | |
| A23K 20/142 | (2016.01) | |
| A61K 31/198 | (2006.01) | |
| A61K 47/24 | (2006.01) | |
| A61K 47/36 | (2006.01) | |

(52) U.S. Cl.
CPC ............... *C05C 11/00* (2013.01); *C05C 3/00* (2013.01); *C05G 3/50* (2020.02); *C05G 5/23* (2020.02); *A23K 20/142* (2016.05); *A23K 20/158* (2016.05); *A61K 31/198* (2013.01); *A61K 47/24* (2013.01); *A61K 47/36* (2013.01)

(58) Field of Classification Search
CPC . A23J 7/00; A23V 2250/06; A23V 2250/063; A23V 2250/1842; A61K 8/553; A61K 9/08; A61K 47/24; A61K 47/44; B01F 2003/0021; B01F 2003/125; B05D 2401/20; B29K 2105/0073; C05G 3/50; C05G 5/27; C05G 5/23; C07C 229/26; Y10S 516/907; C05C 3/00; C05C 11/00
See application file for complete search history.

(56) References Cited

U.S. PATENT DOCUMENTS

| | | | | |
|---|---|---|---|---|
| 2002/0127259 A1* | 9/2002 | Orthoefer | ................. | A23J 7/00 424/409 |
| 2008/0269053 A1* | 10/2008 | Less | ........................... | C05B 7/00 504/101 |
| 2009/0031775 A1* | 2/2009 | Bevans | ..................... | C05C 9/00 71/23 |

OTHER PUBLICATIONS

Ribeiro, Crystallization modifiers in lipid systems, J. Food Sci. Technol., 2014 (Online), 52(7), pp. 3925-3946. (Year: 2014).*

* cited by examiner

*Primary Examiner* — Theodore R. Howell
(74) *Attorney, Agent, or Firm* — Andrew F. Nilles

(57) ABSTRACT

The present invention discloses liquid compositions that include an active compound, water, and means for inhibiting crystal formation or precipitation of the active compound in the liquid composition.

8 Claims, 3 Drawing Sheets

LIQUID PRODUCTS HAVING INCREASED SOLIDS CONCENTRATIONS

CROSS-REFERENCE TO RELATED APPLICATIONS

This application is a national state entry of International Application No. PCT/US2015/064873, filed Dec. 12, 2015, which itself claims priority to U.S. Provisional Patent Application 62/095,431 filed Dec. 22, 2014, each of the contents of the entirety of which is incorporated by this reference.

TECHNICAL FIELD

The present invention relates generally to liquid products. More particularly, the present invention relates to methods of increasing the concentration of solids in a liquid, yet avoiding crystal formation or precipitation.

BACKGROUND OF THE INVENTION

Emulsifiers are amphiphilic molecules that carry a hydrophilic head and a hydrophobic tail. Depending on the charge of the hydrophilic head group, the emulsifiers may be classified as ionic, nonionic, or amphoteric surfactants. The length of the hydrophobic chain also plays a role in quantifying the solubility of the emulsifiers in a given solvent. The solubility of a surfactant may be quantified by a characteristic hydrophile-lipophile balance (HLB) and usually ranges from 1-20, with 1 being more oil soluble and 20 being more water soluble.

The choice of which emulsifier(s) to select in any given system may be, at least in part, determined on whether a water based or an oil based system is being studied. A low HLB emulsifier may be recommended for a water/oil emulsion and a high HLB emulsifier may be recommended for an oil/water emulsion. Some systems may use a mixture of surfactants as single surfactants may not have the desired functionality. Another factor that determines which emulsifier(s) to use is the solubility of the emulsifier.

Lysine is an essential amino acid used in the feed industry to optimize dietary protein. Lysine is the first limiting amino acid in swine nutrition and the second limiting amino acid in poultry nutrition. Various forms of lysine that are commercially available include concentrated liquid L-lysine (base), concentrated liquid L-lysine HCl, L-lysine HCl technically pure, and a monochlorhydrate salt of L-lysine. Each of these forms are considered safe for target species when provided in appropriate amounts.

Liquid lysine in the free base form exists at concentrations of up to 60%. Currently, liquid lysine in free base form is typically sold at 50% because at higher concentrations (i.e., 60%), the liquid lysine will undergo crystallization at ambient temperatures over time. When concentrations of higher than 50% liquid lysine in the free base form are used, feed formulations using such higher concentration liquid lysine require additional moisture and the functional value of such higher concentration liquid lysine in the free base form may be increased. Also, solidification of the liquid lysine in free base form above 50% occurs at temperatures less than room temperature which is an issue in handling and transportation. The 50% concentrations of liquid lysine at temperatures of 20° C. or below will solidify and, thus, require heated storage and transportation facilities.

Due to the aforementioned issues with liquid lysine, liquid L-lysine base is commercially sold at concentrations from 40-50%. Accordingly, liquid lysine products with greater than 50% lysine may be provided in a combination of monochloride and lysine base form.

Changes in the nature of feed products have driven a desire to incorporate liquid actives other than lysine in the feed products for both ease and nutritional benefits. Thus, more concentrated lysine products are desired. Further, liquid lysine products in free base form may be more desired as one report indicated that in a comparison between liquid lysine-free base in the form of monochloride versus a liquid lysine product, the liquid lysine product outperformed the monochloride form in efficacy and bioavailability. (Bioavailability of lysine from a liquid lysine source in chicks; Baker et al.; Poult Sci. 1999; 78(3): 383-6)).

Due to the limited solubility of lysine free base, making a liquid lysine product including lysine free base rather than the hydrochloride form remains a challenge.

SUMMARY OF THE INVENTION

In each of its various embodiments, the present invention addresses these needs and discloses liquid forms of lysine or other active compounds that are more concentrated than liquid lysine or other active compound currently available. The more concentrated liquid lysine or other active compound of the present invention is fluid at lower temperatures and more efficient to transport.

In one embodiment, a liquid composition comprises an active compound, water, and means for inhibiting crystal formation or precipitation of the active compound in the liquid composition. The active compound may be present in the liquid composition at a concentration above a crystallization point of the active compound.

The active compound may be an amino acid, ammonium sulfate, a dried biomass, a bioactive, a nutrient, an antioxidant, a polyol, a protein, a plant residue obtain from removing oil from the plant, and combinations of any thereof. The active compound may be lysine or may be lysine in its free base form. The lysine may be present at an amount of at least 55% by weight, at least 60% by weight, at least 65% by weight, at least 70% by weight, at least 75% by weight, or at least 80% by weight.

The means for inhibiting crystal formation or precipitation of the active compound may be lecithin and may be selected from the group consisting of crude filtered lecithin, fluid lecithin, de-oiled lecithin, chemically modified lecithin enzymatically modified lecithin, standardized lecithin, and combinations of any thereof.

The means for inhibiting crystal formation or precipitation may be present at a concentration of 0.1-5% by weight, at a concentration of between 0.5-4% by weight, at a concentration of between 1-3% by weight, or at a concentration of between 1-2% by weight. The means for inhibiting crystal formation or precipitation may further include a co-emulsifier having an HLB of between 10-18.

In an embodiment, the liquid composition may comprise less than 50% fat. The liquid composition may also include a suspending agent such as a water soluble polymer.

Methods of preventing crystal formation or precipitation of an active compound in a liquid composition are also disclosed. The methods include mixing the means for inhibiting crystal formation or precipitation of the active compound in the liquid composition of the present invention with an active compound, and the active compound may be present in the liquid composition at a concentration above a crystallization point of the active compound.

Uses of the means for inhibiting crystal formation or precipitation of the active compound in the liquid composition of the present invention for inhibiting crystallization of the active compound in a liquid composition comprising water are also disclosed.

In another embodiment, methods of producing the liquid compositions are also disclosed.

DETAILED DESCRIPTION OF THE INVENTION

Figure 1:
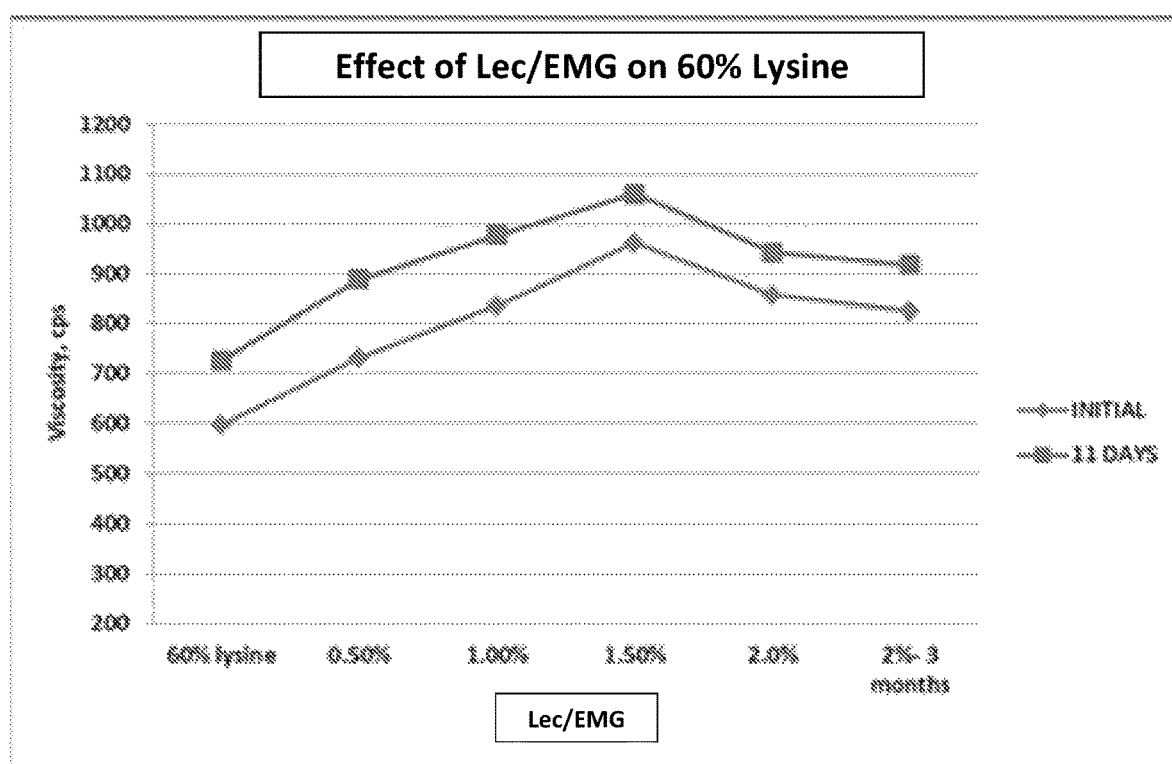
FIG. 1 illustrates viscosities of various embodiments of the present invention.

Disclosed herein are various liquid compositions of the present invention. The liquid compositions may include an active compound, water, and means for inhibiting crystal formation or precipitation of the active compound in the liquid composition. The active compound may be present in the liquid composition at a concentration above a crystallization point of the active compound.

As used herein, the term crystallization point refers to the concentration of an active compound in a liquid composition at which concentration or point the active compound begins to crystallize.

In one embodiment, the liquid composition may comprise less than 50% fat.

In various embodiments, the active compound may be selected from the group consisting of an amino acid, ammonium sulfate, a dried biomass, a bioactive, a nutrient, an antioxidant, a polyol, a protein, a plant residue obtain from removing oil from the plant (i.e., mint plant residue obtained from removing mint oil from portions of a mint plant), and combinations of any thereof. In one embodiment, the active compound is lysine and may be in a free base form.

The means for inhibiting crystal formation or precipitation may be present at a concentration of 0.1-5% by weight, between 0.5-4% by weight, between 1-3% by weight, or between 1-2% by weight. The means for inhibiting crystal formation or precipitation may be lecithin and be selected from the group consisting of crude filtered lecithin, fluid lecithin, de-oiled lecithin, chemically modified lecithin enzymatically modified lecithin, standardized lecithin, and combinations of any thereof.

The liquid composition may further include a suspending agent, such as a water soluble polymer.

In embodiments where the active compound is lysine, the lysine may be present at an amount of at least 55% by weight, at an amount of at least 60% by weight, at an amount of at least 65% by weight, at an amount of at least 70% by weight, at an amount of at least 75% by weight, or at an amount of at least 80% by weight.

In yet a further embodiment, a method of preventing crystal formation or precipitation of a solid compound in a liquid composition includes mixing a means for inhibiting crystal formation or precipitation with the solid, active compound in an aqueous solution.

In order to make lysine or another active compound more concentrated in a liquid, the inventors have discovered that an additive can be added to the liquid to make the lysine or other active compound more concentrated. The additive is thought to act as a crystal inhibitor. In one embodiment, the additive is added to liquid lysine, but in other embodiments, the additive may be added to any liquid containing an active ingredient or used in any application using an active ingredient, wherein the additive enables the solidification properties, crystallization of the active ingredient, or precipitation to be inhibited at higher concentrations.

In one embodiment, the additive used to inhibit crystal formation or precipitation of the present invention is lecithin based. Since lecithin is a natural emulsifier, the lecithin is a good additive for adding to liquid lysine as a feed formulation. Lecithin also is suitable for being compatible with other ingredients that may be added to the liquid lysine as lecithin is a good emulsifier.

Lecithin has traditionally been used as a crystal inhibitor for fat crystallization in fat based systems and confectionaries. Fluid or pumpable shortenings are often used by commercial bakers because of the ease of storage and ability to be metered in a given application. Such fluid shortenings typically contain a solid fat suspended in a liquid medium. A typical formulation may include a hard fat (e.g., lard) and an emulsifier (e.g., lecithin), and is processed through slow cooling of the melted fat, followed by slow and careful agitation. In these fat based systems, lecithin acts as a crystal inhibitor by preventing the co-crystallization of the hard fat triglyceride which keeps the fluid nature of these shortenings for extended periods of time.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0 or 10.0 to 18.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin.

Other co-emulsifiers that may be used include surfactants having an HLB value of between 4-18 or an HLB of between 10-18.

Other additives, in addition to or in place of lecithin, that may be used to inhibit crystal formation or precipitation of an active compound include high HLB emulsifiers. Care must be taken with the high HLB emulsifiers to ensure that air is not incorporated into formulations including the high HLB emulsifiers and does not negatively alter the crystallization characteristics of the active compound. One advantage of the lecithins used to inhibit crystal formation or precipitation of the active compounds of the present invention is that there is less of a concern of producing foam (i.e., incorporating air) in the liquid including the active compound.

Without meaning to be limited by theory, the steric stabilization of the lysine molecule or other active compound with the emulsifier may help avoid flocculation and, thus, eliminate the undesirable crystallization or precipitation of the lysine or other active compound. When lecithin is the emulsifier, an added benefit is that lecithin is a natural emulsifier and provides enhanced fat absorption when used in a feed formulation. The lecithin may also help avoid the fat/oil syneresis or separation of fat or oil present in a liquid feed formulation. Further, where lysine is the active compound, an emulsifier that can dissolve or disperse in a water phase (e.g., lysine in a moisture content of 50%) may be desired.

A co-emulsifier may also be used in combination with the additive for inhibiting crystal formation or precipitation. The co-emulsifier may be an anionic surfactant or a non-ionic surfactant. Such co-emulsifiers include, but are not limited to, polyoxyethylene derivatives of sorbitan monoester, such as a polyethylene oxide of sorbitan fatty acid esters (e.g., sorbitan monopalmitate, sorbitan monooleate, sorbitan monostearate). These compounds are available under the trade name of "TWEEN" of Uniqema Company (a Delaware Corporation) such as TWEEN 60 or TWEEN 80. Any other suitable surfactant in the desired HLB range may be used. Such surfactants are available from numerous suppliers such as, for example, BASF (Florham Park, N.J.), Lonza (Allendale, N.J.), Stepan (Northfield, Ill.), Kerry (Beloit, Wis.).

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, aryl alkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof.

In addition to lysine, in other embodiments the active compound may be ammonium sulfate, other amino acids, polyols, proteins, a plant residue obtain from removing oil from the plant, or any other compound that crystallizes or precipitates in a liquid at a certain concentration of crystallization point. In one embodiment, the active compound is not a fat or an oil, or comprises less than 50% of a fat or oil.

The higher concentration liquids of the present invention may also be used to suspend more than one active compound in the liquid. In addition to one active compound, additional solids may be added to the compositions in order to make the higher concentration products more functional. The compounds that may be used include, but are not limited to, a dried biomass, bioactives, nutrients, antioxidants, and combinations of any thereof.

In another embodiment, a suspending agent may be added to the compositions of the present invention. Non-limiting examples of suspending agents include water soluble polymers, gums (i.e. such as xanthan gum), clay, kaolinite, smectite, vermiculite, aluminosilicate clay, attapulgite clay, pectin, microcrystalline cellulose, carrageenan, acacia, agar, guar, locust bean gum, tragacanth, starch, dextrins, or any combinations thereof. The suspending agent may be added at concentrations ranging from 0-5%.

The present invention is further demonstrated by the examples that follow.

Example 1

An emulsifier was incorporated into a liquid containing an active compound. In this manner, the dry solids content of the active compound in the liquid may be increased and flowability may be maintained.

Varying amounts of lecithin were added to an amount of 50% liquid lysine to achieve 0.5%, 0.75%, and 1.0% by mass of lecithin in the 50% liquid lysine. The resulting combination was mixed. In order to show the ability of the lecithin to inhibit crystal formation or precipitation of the 50% liquid lysine as the solids content increased, the resulting combination was evaporated in a natural convection evaporator until the viscosity increased, at which point the evaporation was ceased and product was collected.

Example 2

Combinations of liquid lysine and varying concentrations of lecithin were mixed substantially in the same manner as described in Example 1 using a fluid lecithin and 50% liquid lysine. After mixing, the liquid lysine concentration was increased to about 60% by evaporation. The concentrations of lecithin used were 0.5%, 1.0%, 1.5%, and 2.0%. The fluid lecithin includes lecithin blended with a co-emulsifier (i.e., ethoxylated monoglycerides) and has an HLB of about 12. In this example, the lecithin was shown to inhibit crystallization in the 60% lecithin.

FIG. 1 shows the effect of the concentration of the fluid lecithin on the viscosity of 60% lysine initially and at 11 days, and in the case of 2% lecithin/ethoxylated monoglyceride, after 3 months. The graph of FIG. 1 illustrates that the lecithin is able to inhibit the crystallization of 60% lysine.

Figure 2:
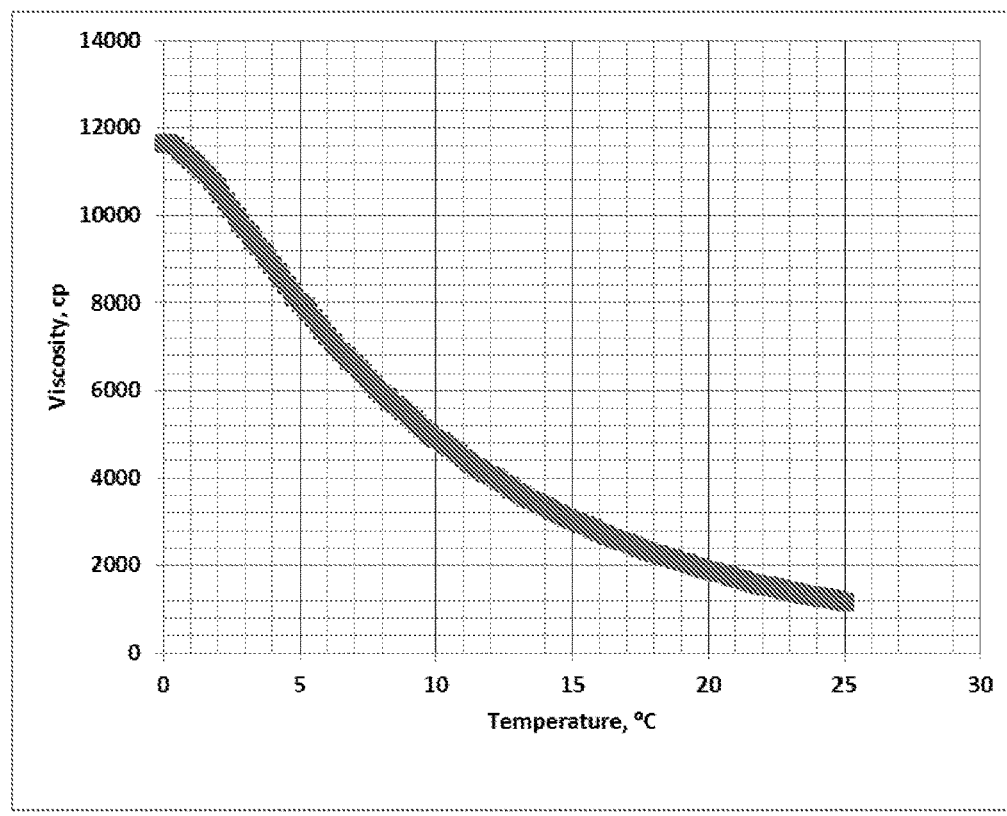
FIG. 2 shows the viscosity of another embodiment of a liquid composition of the present invention.

The concentration of the lysine was also increased to more than 70% using the lecithin at 1.5% and the effect of viscosity as a function of temperature of the 70% lysine was determined and shown in the graph of FIG. 2.

Figure 3:
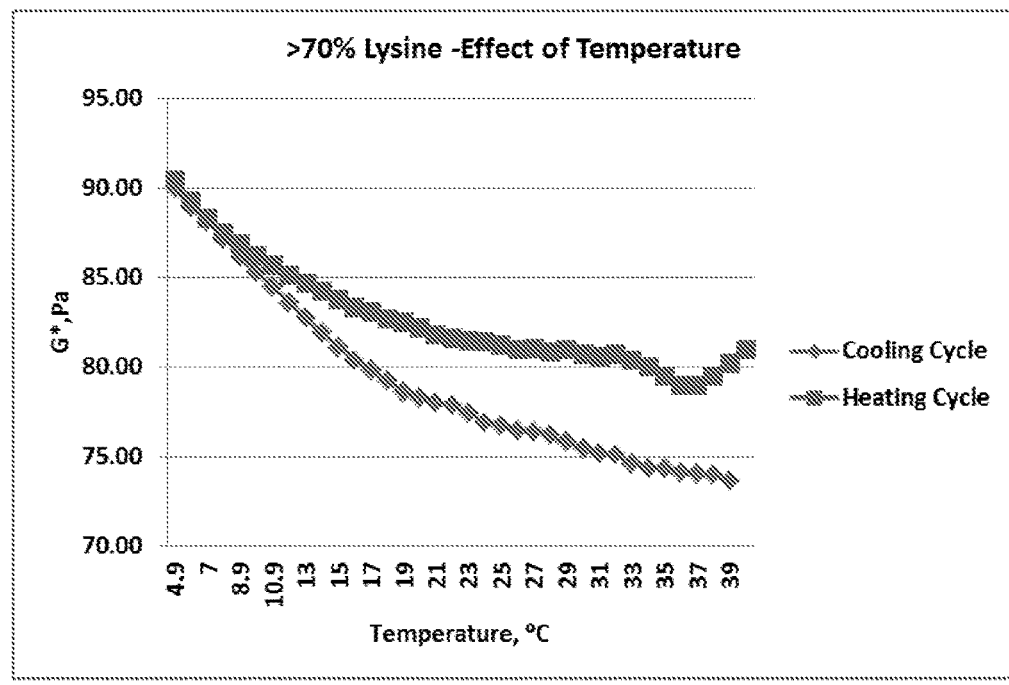
FIG. 3 depicts the ability of an additional embodiment of the present invention to resist crystal formation over a temperature range.

The viscosities of the 70% lysine product going through various heating and cooling cycles were also determined with oscillatory measurements. The measurements were done from about 5° C. to about 40° C. and the complex modulus, G*, was measured as a function of temperature. As shown in the graph of FIG. 3, the heating and cooling of the lysine with lecithin/ethoxylated monoglyceride does not significantly affect the crystallization properties.

Example 3

The ability of the combination of lecithin and the co-surfactant polysorbate 80 (i.e., polyoxyethylene sorbitan monooleate, PS 80) and ethoxylated monoglycerides (EMG) was evaluated for its ability to inhibit the crystallization of lysine. Fluid lecithin was used in this Example. The fluid lecithin includes lecithin blended with a co-emulsifier (i.e., polysorbate 80) and has an HLB of about 15.

Table 1 shows the assay values for the various lysine treatments using different concentrations of lecithin in this Example.

TABLE 1

| Sample | Lysine-HCl (g/L) | Lysine (g/L) | Total Solids (%) | Moisture (%) |
|---|---|---|---|---|
| Control | 767.0 | 613.6 | 66.1 | 33.9 |
| 0.5% lec/PS 80 | 739.6 | 591.7 | 65.4 | 34.6 |
| 0.75% lec/PS 80 | 741.1 | 592.9 | 66.1 | 33.9 |
| 1.0% lec/PS 80 | 771.1 | 616.9 | 68.0 | 32.0 |
| 1.0% lec/EMG | 778.8 | 623.0 | 70.2 | 29.8 |

Figure 4:
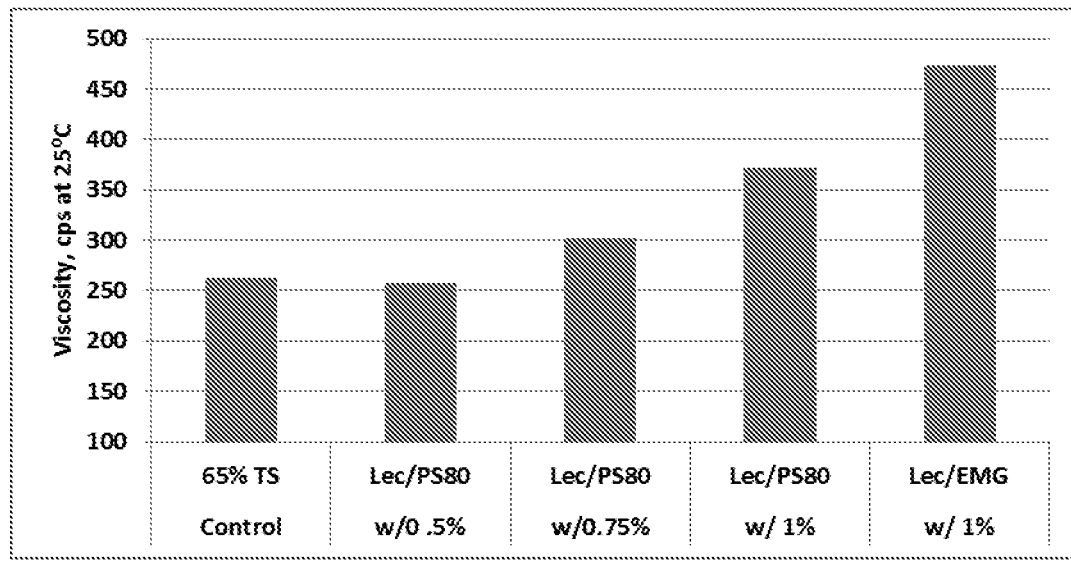
FIG. 4 shows the viscosity profile of various embodiments of the present invention.

FIG. 4 shows the viscosity at 25° C. of the samples of Table 1. As shown in FIG. 4, at equal concentrations, the lecithin with the polysorbate had a relatively lower viscosity than the lecithin with the ethoxylated monoglycerides.

Example 4

The viscosity of the greater than 60% lysine is slightly higher than the viscosity of 50% lysine. The higher viscosity enables the higher lysine concentration to be able to suspend additional solids in solution. One solid that may be suspended in the solution is a dried threonine biomass. The dried threonine biomass may be suspended in the lysine solution alone or in combination with a water soluble polymer, such as xanthan gum. The dried biomass may be added at concentrations of up to 5% and the water soluble polymer may be used in concentrations of up to 2%.

Figure 5:
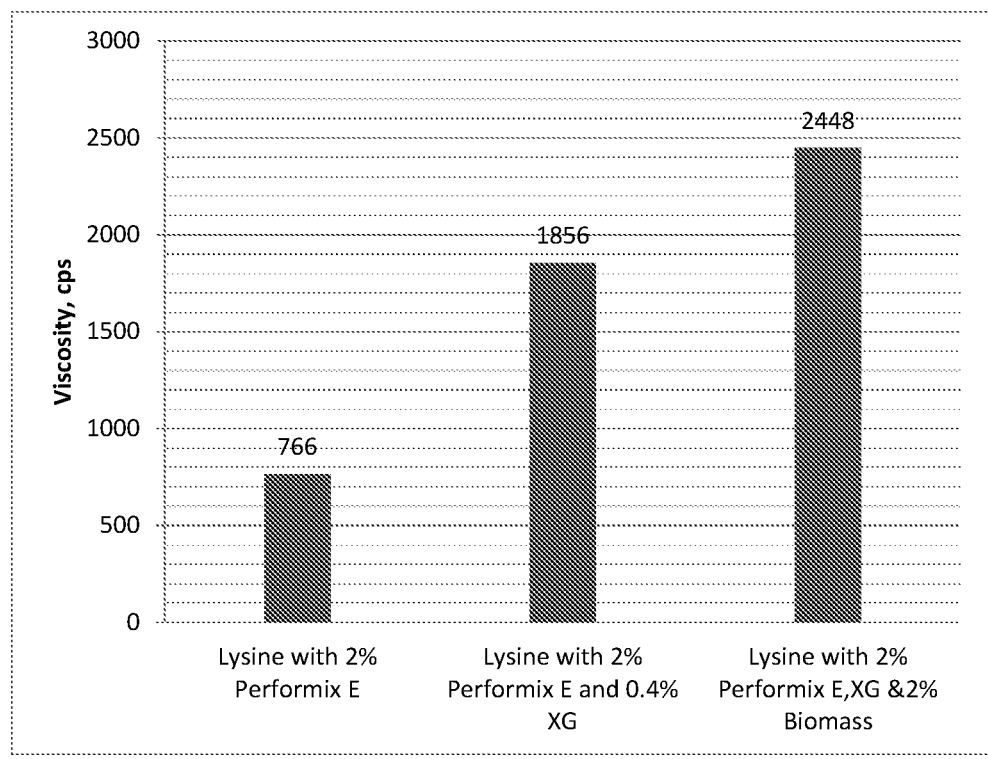
FIG. 5 illustrates viscosity profiles of additional embodiments of the present invention.

FIG. 5 shows the viscosity of 50% lysine with 2% added lecithin, 50% lysine with 2% added lecithin/EMG and 0.4% xanthan gum, and 50% lysine with 2% lecithin/EMG, xanthan gum, and 2% of a dried biomass.

Example 5

The ability of the additive of the present invention to function to prevent crystallization was assessed with an ammonium sulfate solution, which in this embodiment is a by-product of lysine production. A control sample of about 35% ammonium sulfate was used as a starting point and 3 emulsifiers were added, and the combination of ammonium sulfate and emulsifier was concentrated to have a solids content of at least 50%. As shown in Table 2, the presence of the emulsifiers were able to maintain fluidity of the concentration of ammonium sulfate of more than 50%. Emulsifier 1 is a lecithin/fatty acid ethoxylate blend. Emulsifier 2 is a lecithin/alkyl polyglycoside blend. Emulsifier 3 is a lecithin/fatty acid ethoxylate blend in the presence of a lactic acid/sodium lactate buffer.

TABLE 2

| Sample | % water | % dry solids | settling |
|---|---|---|---|
| Control | 69.5 | 30.5 | No settling |
| Emulsifier 1 | 41.6 | 58.4 | Some settling |
| Emulsifier 2 | 44.8 | 55.2 | No settling |
| Emulsifier 3 | 46.2 | 53.8 | No settling |

The present invention has been described with reference to certain exemplary and illustrative embodiments, compositions, and uses thereof. However, it will be recognized by persons having ordinary skill in the art that various substitutions, modifications or combinations of any of the exemplary embodiments may be made without departing from the scope of the invention. Thus, the invention is not limited by the description of the exemplary and illustrative embodiments, but rather by the appended claims.

What is claimed is:

1. A method of preventing crystal formation or precipitation of an active compound in a liquid composition, the method comprising:
   mixing a means for inhibiting crystal formation or precipitation of an active compound in an aqueous solution with water and the active compound;
   wherein the active compound is present in the liquid composition at a concentration above the crystallization point of the active compound;
   wherein the active compound is selected from the group consisting of an amino acid, ammonium sulfate, and a combination thereof; and
   wherein the liquid composition comprises less than 50% fat.

2. The method of claim 1, wherein the means for inhibiting crystal formation or precipitation of the active compound is lecithin.

3. The method of claim 2, wherein the active compound is lysine.

4. The method of claim 3, wherein the lysine is in a free base form.

5. The method of claim 1, further comprising mixing a dried biomass with the liquid composition.

6. The method of claim 1, wherein the means for inhibiting crystal formation or precipitation is present at a concentration of 0.1-5% by weight, at a concentration of between 0.5-4% by weight, at a concentration of between 1-3% by weight, or at a concentration of between 1-2% by weight.

7. The method of claim 1, further comprising mixing further comprising mixing a suspending agent in the liquid composition.

8. The method of claim 1, wherein the active compound is lysine and is present at an amount of at least 55% by weight, at least 60% by weight, at least 65% by weight, at least 70% by weight, at least 75% by weight, or at least 80% by weight.

* * * * *